United States Patent [19]

Okimoto

[11] Patent Number: 4,784,158
[45] Date of Patent: Nov. 15, 1988

[54] VAGINAL TESTING APPLICATOR AND METHOD

[76] Inventor: Paul M. Okimoto, 638 Cornell, Albany, Calif. 94706

[21] Appl. No.: 87,807

[22] Filed: Aug. 21, 1987

[51] Int. Cl.$^4$ ............................................. A61B 5/00
[52] U.S. Cl. .................................... 128/771; 128/759; 604/16; 604/55; 604/271
[58] Field of Search ............... 128/632, 636, 736, 738, 128/759, 769, 771; 604/1, 12, 15, 16, 18, 54, 55, 171, 181, 271

[56] References Cited

U.S. PATENT DOCUMENTS

| | | | |
|---|---|---|---|
| 3,037,496 | 6/1962 | Melges | 128/636 |
| 3,589,356 | 6/1971 | Silverman | 604/54 |
| 3,598,533 | 8/1971 | Tomioka et al. | 128/636 |
| 4,164,212 | 8/1979 | Schuster | 128/759 |
| 4,324,262 | 4/1982 | Hall | 128/759 |
| 4,344,439 | 8/1982 | Jacebellis | 128/771 |
| 4,496,341 | 1/1985 | Brucks | 604/15 |
| 4,586,604 | 5/1986 | Alter | 128/759 |
| 4,619,271 | 10/1986 | Buyer et al. | 128/736 |

FOREIGN PATENT DOCUMENTS 142903  7/1903  Fed. Rep. of Germany ........ 604/15

Primary Examiner—Max Hindenburg
Attorney, Agent, or Firm—Flehr, Hohbach, Test, Albritton & Herbert

[57] ABSTRACT

An applicator assembly and method for self-testing a body cavity to determine the condition therein is disclosed. The assembly includes a reusable, applicator body, formed with a probe having a tip end formed and positioned for movement between a retracted position and an extended position. Removably mounted thereon is a flexible sheath, which carries a sensor proximate the end of the sheath. Upon movement of the probe to the retracted position, the sensor and sheath are drawn into the applicator body to protect the sensor from contamination before testing. The assembly is then inserted into the cavity, the probe is extended for testing and retracted for removal of the assembly from the cavity. To observe the test results, the probe is again extended. The sheath is removable and a new sheath can be mounted over the applicator body for repeated testing. A method of self-testing, using the assembly of the present invention is also provided.

13 Claims, 2 Drawing Sheets

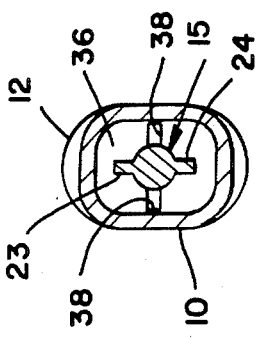
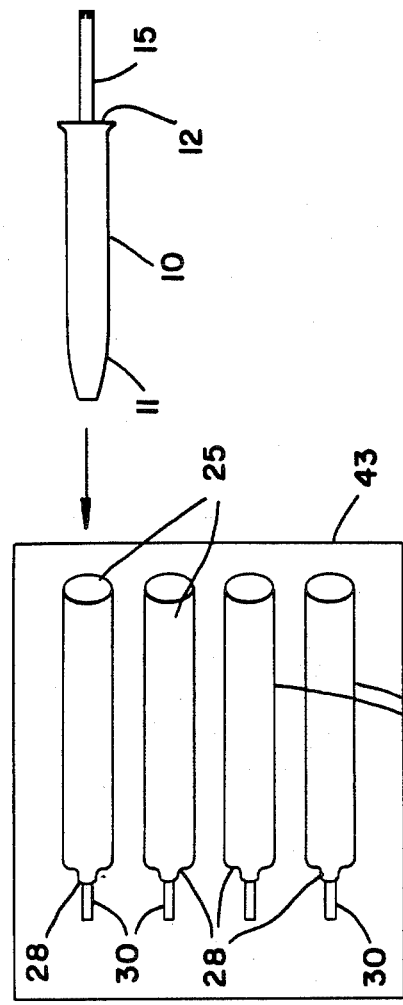
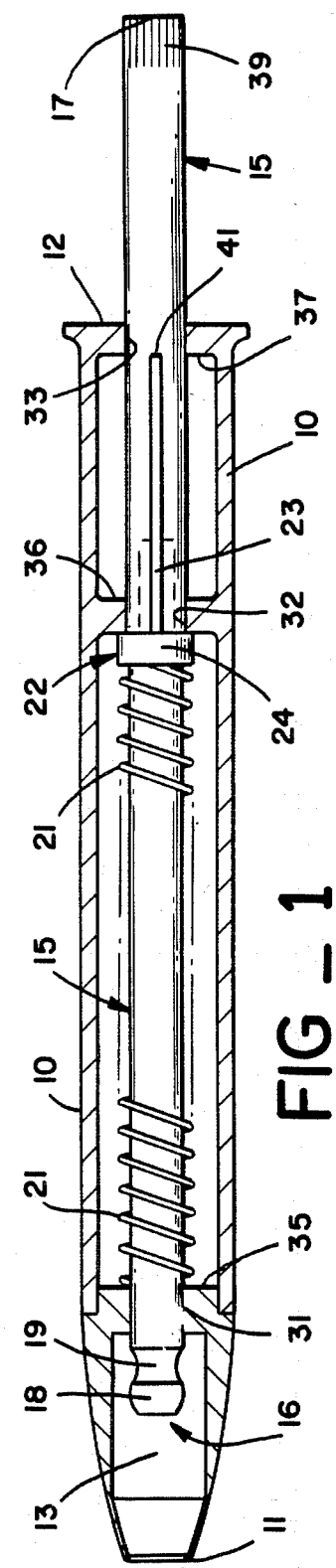

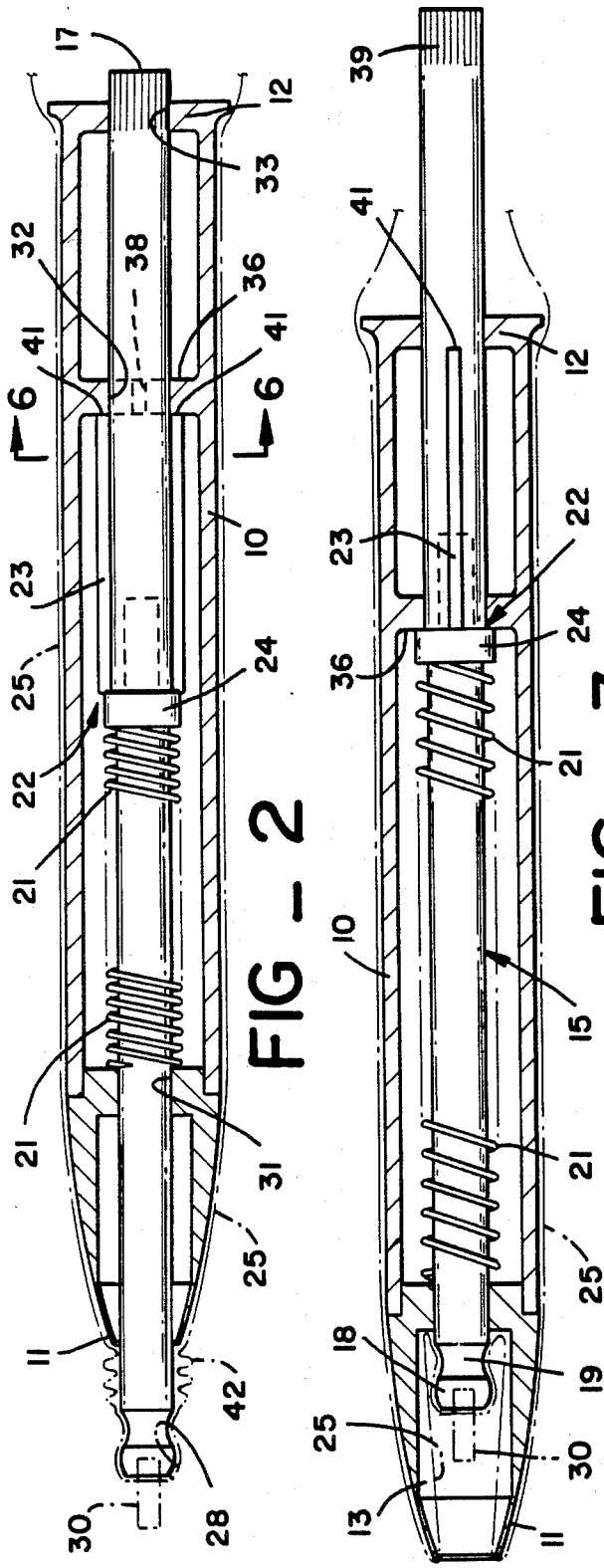

VAGINAL TESTING APPLICATOR AND METHOD

BACKGROUND OF THE INVENTION

This invention relates to a method and apparatus for testing a body cavity to determine the condition therein. More particularly, this invention provides a method and apparatus for determining the acidity level of the vagina.

Typically, the vagina of a healthy human female has a pH of less than 4.5. It is well known that an elevated pH occurs among women with a variety of bacterial infections. Determining the pH level of the vagina is usually done by a doctor or clinician in a doctor's office because false readings are easily obtained if the procedure is not carried out properly, e.g., if the pH paper used comes in contact with cervial secretions or urine. Such contact can yield false pH readings in the high range, possible provoking an unnecessary visit to a doctor's office, or in the low range, yielding a false negative response which could result in a delay in treatment with serious consequences.

There are no self-testing devices presently used as a result of this contamination problem. Accordingly, it would be advantageous to provide a reusable vaginal testing applicator assembly which would minimize the hazard of obtaining false readings through contact with contaminating substances.

One prior attempt to provide a vaginal testing applicator including an applicator body having an element retractably mounted therein to which pH paper was mounted. The paper was retracted inside the body of the applicator during insertion and removal from the vagina so that the paper would not be contacted by urine or cervical fluids. When inserted the element would be extended to contact the pH paper with fluids in the center one-third of the vagina so that a pH level could be determined. While operable, this prior art device has the disadvantage that it must be carefully cleaned after each use, making self-use by clinically untrained personnel unreliable and potentially hazardous.

SUMMARY OF THE INVENTION

The assembly of applicant's invention permits self-testing of the vaginal pH level by untrained personnel, and it is reusable, thereby providing an economically advantageous alternative to other devices and methods known to applicant. The applicator assembly includes an elongated applicator body dimensioned to be received within a body cavity and having a length sufficient for positioning the front end of the applicator body within the cavity beyond the external walls thereof with the opposite end proximate the entrance to the cavity. The applicator body is further formed with a probe element having a tip end, the probe being formed and positioned within the applicator body for movement of the tip end between a retracted position within the applicator body and an extended position outward of the applicator body.

Removably mounted over the front end of the applicator body and formed for embracement of the tip end of the probe in an extended position and for adherence to the tip end upon movement of the probe to the retracted position, is a flexible sheath. A sensor to detect a condition within the body cavity is carried by the sheath proximate securement of the sheath to the tip end of the probe.

In one embodiment of the invention, the applicator body is dimensioned for insertion into the human vagina and has a length sufficient to position the front end of the applicator body proximate the center one-third of the vagina. In this embodiment the flexible sheath is formed with a closed end embracing the tip end of the probe and adhering thereto upon movement of the probe from the extended position to the retracted position, and the sensor used to detect the condition of the vagina is a strip of litmus paper.

Prior to the insertion of the applicator assembly into the body cavity, the applicator body is inserted into the flexible tubular sheath and the sheath is secured to the end of the retractable probe by extending the tip end of the probe out into a resiliently deformable pocket in the end of the sheath. The probe is retracted with the sheath frictionally secured thereto until the sensor is inside the applicator body, thereby protecting the sensor from contact with objects and substances that could give false readings. The assembly may be inserted into the cavity, and the probe is extended beyond the front end of the applicator body to expose the sensor to the interior of the cavity, and to contact the sensor with a cavity wall or fluids in the cavity. After contact the probe is retracted into the applicator body, which is withdrawn from the cavity, again without contacting the sensor with the passageway to the cavity. The probe is then placed in the extended position to observe the sensor and determine the condition of the cavity. After use of the applicator assembly, the sheath and sensor can be stripped from the applicator body, which has not been exposed to or contaminated by contact with the cavity or passageway to the cavity. The applicator can be washed with soap and water, and a new sheath thereafter can be mounted over the applicator body and secured to the retractable probe.

Accordingly, it is an object of the present invention to provide a body cavity self-testing device that is accurate, can be used by relatively untrained users, and is reusable.

It is another object of the present invention to provide a vaginal testing applicator which is simple and inexpensive to construct and use.

It is also an object to provide a vaginal self-testing device and method that minimizes the possibility of false sensor readings due to improper contact of the sensor with contaminants.

BRIEF DESCRIPTION OF THE DRAWINGS

FIG. 1 is a longitudinal view in cross-section of the applicator body of a cavity testing applicator assembly constructed in accordance with the present invention with the probe in a retracted position.

FIG. 2 is a longitudinal view in cross-section of the assembly of the present invention with the probe in an extended position for mounting of a sheath, shown in phantom, thereon.

FIG. 3 is a view corresponding to FIG. 2, with the probe in the retracted position.

FIG. 4 is a view corresponding to FIG. 2 with the probe in an extended position for contact with a cavity wall.

FIG. 5 is a reduced, plan view of a self-testing applicator kit constructed in accordance with the present invention.

FIG. 6 is a cross-sectional view taken substantially along the plane of line 6—6 in FIG. 2.

DETAILED DESCRIPTION OF THE INVENTION

Referring to the drawings, there is shown the applicator assembly of the present invention including applicator body 10, probe means, generally designated 15, sheath means, generally designated 25, and sensor means 30 (see FIG. 2).

Applicator body 10 is elongated and tubular in construction, having a narrowed, cone-shaped front end 11 and a flanged opposite end 12. Flanged end 12 enables gripping of body 10 between the index and middle fingers and operation of probe means 15 by engaging the end 17 of the probe with the user's thumb or a finger on the other hand. When used as a vaginal self-testing applicator, body 10 has a length and diameter slightly larger than a typical ball point pen. More particularly, body 10 has a length sufficient for positioning front end 11 within the cavity to be tested with opposite end 12 proximate and preferably outside the entrance to the passageway to the body cavity. As best may be seen in FIG. 6, body 10 preferably is formed with oval shaped cross-section to enhance manual manipulation of the applicator assembly.

In order to permit shielding of sensor means 30 within body 10, a recess or cavity 13 is formed in the front end 11 of the body which is dimensioned to receive probe means 15 with sheath means 25 and sensor 30 mounted thereon, as will be fully described below.

Elongated probe means 15 is movably positioned within body 10 and includes tip end, generally designated 16, positioned near front end 11 of the body. Tip end 16 is formed with distal end or head portion 18 at the outermost end of probe means 15 and neck portion 19 immediately behind head portion 18 and terminates in a manually engageable opposite end 17. Probe 15 is slidably mounted in bores 31, 31 and 33 in transverse walls 35, 36 and 37, respectively, in applicator body 10. This configuration enables the probe element to be moved between a retracted position within body 10, such that tip end 16 is contained within recess 13 (FIGS. 1 and 3), and an extended position, such that tip end 16 is extended outward of body 10 beyond front end 11 (FIGS. 2 and 4).

The vaginal applicator assembly of the present invention includes a probe extension and retraction mechanism. More particularly, spring means 21 may be concentrically mounted to probe 15 between transverse wall 35 of the applicator body and a collar or shoulder 24 on probe 15. Since spring 21 is most preferably a compression spring, the spring will bias probe 15 to the retracted position of FIGS. 1 and 3, and collar 24 will be urged against wall 36.

In order to enable locking of probe 15 in the extended position of FIG. 2 against the spring biasing force of spring 21, the extension and retraction mechanism further preferably includes locking means, generally designated 22. Locking means 22 advantageously includes a longitudinally extending projection or fin 23 (most preferably a fin 23 on each side of probe 15) which slidably mates with slots 38 in wall 36 (see FIGS. 2 and 6). Fins or projections 23 and slots 38 in wall 36 are positioned so that upon movement of the probe to the extended position by pressing on end 17 of the probe, projections 23 pass beyond slotted wall 36 while end 17 is still outwardly of flanged end 12 of the applicator body. Knurling 39 on end 17 of the probe can then be used to rotate the probe so that the ends 41 of projections 23 bear against wall 36 and lock the probe in the extended position of FIG. 2 against compression spring 21.

To release probe means 15 from the extended position, the user turns end 17 so that projections 23 line up with slots 38 in bore 32. Spring means 21 then urges projections 23 through slotted bore to thereby move probe means 15 to the retracted position.

As thus far described in detail, the applicator assembly includes structure which is broadly known in the prior art. Such prior art cavity testing apparatus have not, however, provided a self-testing system which is easily reusable. In order to provide a hygienically acceptable reusable applicator, the present applicator includes sheath means 25 which is formed and dimensioned for mounting over applicator body 10. Mounted to the exterior of sheath or sleeve 25 proximate an end thereof is sensor means 30, which in the case of a vaginal self-testing applicator may advantageously be a small strip of litmus or pH paper which is adhesively secured to the sheath.

In order to secure sheath 25 to the applicator, probe 15 is locked in the extended position of FIG. 2 and then the tip end 16 of the probe is jammed or forced into the closed end of the sheath. Since the sheath is preferably formed of a thin, deformable plastic, tip end 16 and particularly head portion 18 can be urged into the plastic sheath which will deform and then resiliently contract down against neck portion 19 of the probe to frictionally secure the sheath to the prove. This process of securing the sheath to the probe is enhanced if sheath 25 includes a preformed pocket 28 dimensioned to be slightly smaller than head portion 18 so that pocket 28 can be urged over head 18 and will resiliently contract slightly in the area of neck 19 to secure the sheath to the probe and applicator assembly.

As will be seen, sheath 25 preferably has a length dimension which extends over the full length of body 10 so as to shield the applicator body against contact with the body of the user. Thus, sheath 25 maintains the hygienic integrity of the applicator assembly and allows the applicator body to be reused with other sheaths without the need for special cleaning of the applicator, although washing with soap and water after use is recommended.

As can be seen in FIG. 2, the sheath is preferably formed so that where it is urged over tip end 16, there is some extra material left just in front of conical end 11 of the applicator body. Thus, a plurality of folds 42 are shown in FIG. 2 to permit further manipulation of the sheath as described below.

Upon securement of sheath 25 to probe 15, the probe is moved to the retracted position, which movement causes pocket 28 of sheath means 25 and sensor means 30 to be retracted into recess 13, as shown in FIG. 3. Folds 42 in FIG. 2 can be seen to have provided sufficient material to permit retraction of the pocket and sensor into cavity 13 without pulling the sheath off the probe. The assembly then may be inserted into the body cavity to be tested, for example, the vagina, and the probe again is moved to an extended position, as shown in FIG. 4. In a particular embodiment illustrated, it envisages that the level of acidity in the human vagina is to be tested. In this embodiment, therefore, applicator body 10 has a length sufficient to position front end 11 proximate the middle one-third of the vagina, and sensor means 30 comprises a strip of litmus paper. Upon movement of the probe means to the extended position of FIG. 4, litmus paper 30 will extend outward of front end 11 and contact an interior wall of the vagina. As will be noted by comparing FIGS. 2 and 4, end 17 of the probe is depressed in FIG. 4 until knurled portion 39 reaches end wall 37. In this position ends 41 of fins 23 have not passed beyond slotted wall 36 so that the probe is not locked in the extended position.

After contact of litmus paper 30 with a vaginal wall and/or fluids, probe means 15 is retracted by releasing the pressure one end 17 of the probe, and the applicator assembly is removed from the vagina. As will be seen, therefore, during insertion of the applicator assembly into the vagina, retraction of the sheath and litmus paper into recess or cavity 13 shields the litmus paper from contact with cervical fluids and urine which could produce false test results. Similarly, after contacting the vaginal walls, the litmus paper is retracted into cavity 13 before withdrawing the applicator so that the litmus paper is shielded again from contact with the cervix.

Once the applicator is removed from the vagina, probe 15 can be moved to either of the extended positions shown in FIGS. 2 and 4, and the acidity of the vagina determined by observing the litmus paper. Once the test is complete sheath 25 can be stripped from the applicator by pulling the sheath off of the head of the probe to permit the applicator to be reused, usually after washing with soap and water.

Sheath means 25 is preferably formed of resiliently deformable plastic or rubber-based material, such as polyethylene or latex-based material. The sheath is preferably relatively thin walled to enhance flexibility and adherence to tip end 16. As will be understood, however, the sheath can be secured to probe 15 in other manners, and flexibility need only be sufficient to enable the sheath to be pulled down inside the applicator body cavity 13.

Sensor means 30 is most preferably litmus or pH paper. As will be understood, however, other sensors can be employed. In a doctor-employed version of the applicator assembly, for example, sensor 30 can be electrical sensing apparatus, such as a pair of contacts, which can be used to read-out pH to a metering device. The contacts would be mounted to the exterior of a disposable sleeve or sheath and would be retracted inside the applicator body during the insertion process. Retraction during removal would not be as critical since a reading could be taken before removal. Moreover, for testing of conditions within a body cavity other than acidity, sensor 30 would take a form appropriate to the test being conducted.

The present invention also includes a kit (FIG. 5) comprising applicator and a plurality of sheath means 25 each having sensors 30 mounted thereto, for repeated self-testing of a body cavity. The sleeves advantageously may be removably secured to a card or other carrier 43 and they have preferably been sterilized and packaged with a covering sheet, not shown, which will resist contamination.

Because only sheath means 25 and sensor means 30 must be discarded after use, the assembly of the present invention provides an economical, body cavity testing applicator assembly which is hygienic and reliable.

What is claimed is:

1. An applicator assembly for self-testing of a body cavity for the detection of a condition in said cavity including an elongated applicator body dimensioned to be received within said body cavity and having an open front and a length sufficient for positioning of said open front end of said applicator within said cavity beyond the external walls thereof; probe means having a tip end, said probe means being formed and positioned within said applicator body for movement of said tip end between a retracted position within said applicator body and an extended position outward of said open front end of said applicator body;

flexible sheath means having a closed end and removably mounted and extending over said open front end of said applicator body to prevent the entry of contaminates in said front end, wherein the improvement in said applicator assembly comprises said sheath means extending across said tip end and being removably attached to said tip end for movement therewith between said extended position and said retracted position; and sensor means to detect a condition within said body cavity and carried by said sheath means for movement therewith on an exterior side of said sheath means proximate attachment of said sheath means to said tip end and said sensor means being dimensioned for retraction inside said applicator body through said open fron end.

2. The applicator assembly as defined in claim 1 wherein, said probe means includes spring means formed to bias said tip end in said retracted position, locking means formed for releasable securement of said tip end in said extended position, and said probe means and said sheath means being cooperatively formed for removably mounting of said sheath means to said tip end for adherence of said sheath means to said tip end.

3. The applicator assembly as defined in claim 2 wherein, said locking means includes a longitudinal projection on said probe means and a mating, slotted opening in said applicator body formed for receipt and passage of said projection beyond said opening upon movement of said tip end to said extended position to enable releasably locking of said probe means upon rotation of said probe means about the longitudinal axis of said applicator.

4. The applicator assembly as defined in claim 1 wherein, said sensor means is a strip of litmus paper.

5. The applicator assembly as defined in claim 1, wherein, said probe means includes locking means formed to enable selective locking of said probe means in said extended position.

6. The applicator assembly as defined in claim 1 wherein, said tip end is formed with a head portion and a neck portion at a distal end thereof, and said sheath means is resiliently deformed over said distal end and said neck to attach said sheath means to said tip end.

7. The applicator assembly as defined in claim 6 wherein, said sheath means is formed to define a pocket dimensioned to mate with and be resiliently deformed over said distal end.

8. A sheath for use with an applicator having a body to enable periodic self-testing of a body cavity for the detection of pathogens or the like comprising:

a tubular member having an internal diameter dimension for sliding engagement over at least a portion of said applicator body and having a closed end, said end being sufficiently flexible to permit said end to be inverted and pulled down inside said tubular member; and sensor means attached to an exterior side proximate said closed end of said tubular member dimensioned to be positioned inside said tubular member when said tubular member is inverted and formed for detection of a condition in said body cavity.

9. A sheath as defined in claim 8 wherein,
said sensor means is litmus paper.

10. A sheath as defined in claim 8, and
a plurality of sheaths each formed in the same manner as the first named sheath and each being removably secured to a carrier means.

11. A self-testing kit for the measurement of the acidity of the human vagina comprising:

an elonged applicator body having an open front end and dimensioned for insertion into said vagina and having a length sufficient to position said open front end thereof proximate the center one-third of the vagina;

a plurality of sheath means formed for removably mounting over said open front end of said applicator, said sheath means having a closed end thereof dimensioned to extend across said open front end; and a strip of litmus paper carried by each of said sheath means at said closed end on an exterior side of said sheath means.

12. The kit as defined in claim 11 wherein, said elongated applicator includes probe means having a tip end and being formed and positioned within said applicator body for movement of said tip end between a retracted position within said applicator body and an extended position outward of said applicator body, said sheath means being formed for releasably attachment to said tip end for movement therewith, and said open front end dimensioned for receipt of said sheath means and said litmus paper inside said applicator body in said retracted position.

13. A method of self-testing of a body cavity for the detection of pathogens or the like including the steps of inserting an applicator assembly including an applicator body, a retractable probe means mounted in said body and sensor means carried by said probe means into said cavity, and extending the retractable probe means beyond the front end of said applicator body to contact the cavity wall with said sensor means, wherein the improvememnt in said method comprises the steps of:

prior to said step of inserting said applicator body into said cavity, inserting said applicator body into a flexible tubular sheath means having a closed end and said sensor means carried by an exterior surface of said sheath means proximate said closed end, said sheath means having a length extending over substantially the entire length of said applicator body, securing said sheath means to an end of said retractable probe means for movement therewith, and retracting said probe means with said sheath means secured thereto until said sensor means is inside said applicator body prior to insertion into said cavity.

* * * * *